United States Patent [19]

Gaffar

[11] 4,272,513

[45] Jun. 9, 1981

[54] STABILIZED ORAL COMPOSITION

[75] Inventor: Abdul Gaffar, Somerset, N.J.

[73] Assignee: Colgate-Palmolive Company, New York, N.Y.

[21] Appl. No.: 117,156

[22] Filed: Jan. 31, 1980

[51] Int. Cl.$^3$ .......................... A61K 7/16; A61K 7/18
[52] U.S. Cl. ....................................... 424/52; 424/49; 424/58
[58] Field of Search .................................... 424/49–58

[56] References Cited

FOREIGN PATENT DOCUMENTS 2208055 9/1972 Fed. Rep. of Germany.
47-01479 1/1972 Japan.
49-39818 10/1974 Japan.

OTHER PUBLICATIONS

Chem. Abstracts 83 #33030b (1975) of Japan No. 7439818 Iwasaki et al.
Chem. Abstracts 78 #47669A (1973 of Okano et al., Japan No. 72/01479 Jan. 14, 1972.
Chem. Abstracts 77 #1438039 (1972) of Hurica Ger. Offen. No. 2,208,055, Sept. 7, 1972.
Jacobs Am. Perf. 61:469–471 Flavoring Mouthwashes Jun. 1953.
Jacobs Am. Perf. 61:389,391,393 How To Flavor Toothpaste May 1953.

Primary Examiner—Shep K. Rose
Attorney, Agent, or Firm—Herbert S. Sylvester; Murray M. Grill; Robert L. Stone

[57] ABSTRACT

An oral composition containing an oral vehicle, tranexamic acid as antigingivitis agent, a fluorine-containing anticaries agent, and a flavor mixture of methyl salicylate, menthol, eugenol and cineol.

7 Claims, No Drawings

STABILIZED ORAL COMPOSITION

This invention relates to an oral composition which promotes oral hygiene, and especially to such a composition for treating and controlling certain periodontal diseases, for example inflammation, bleeding and/or swelling of the gums as in gingivitis and parulis, gingival retraction, ulatrophy, etc, in addition to inhibiting the formation of caries.

Periodontitis, or pyorrhea, is a disease affecting the supporting tissues of the teeth including the gingiva, the membrane lining the sockets which the teeth lie, and the bones surrounding the teeth. The disease may initially be associated with conditions of constant irritation of the gingiva by dental plaque, food impaction, poor dental restorations, traumatic occlusion, or chemical irritants.

The gums may be seriously harmed by deposits of dental plaque, a combination of minerals and bacteria found in the mouth. The bacteria associated with plaque can secrete enzymes and endotoxins which can irritate the gums and cause an inflammatory gingivitis. As the gums become increasingly irritated by this process they have a tendency to bleed, lose their toughness and resiliency, and separate from the teeth, leaving periodontal pockets in which debris, secretions, more bacteria and toxins further accumulate. It is also possible for food to accumulate in these pockets, thereby providing nourishment for increased growth of bacteria and production of endotoxins and destructive enzymes. The pus that forms in this process is capable of destroying gum and bone tissue. A variety of bacteria are generally found to be present during the active stages of periodontal disease. Such organisms as streptococci, staphylococci and gram negatives are usually present, and are found in the purulent discharge as well as in the involved tissue, and may be absorbed into the general system through the lymphatics or venous blood stream.

The progression of the pyorrheic process usually begins with gingivitis, initiating at the margins of the gums, in which the gingiva become more tender and sensitive, and appear flabby, inflamed and swollen. Periodontal pockets become apparent, and infection takes place in these pockets. Effective control and prevention of gingivitis accordingly constitutes a desideratum for the prevention of further periodontal diseases.

A multitude of materials have been previously proposed and employed for controlling oral diseases and malfunctions such as plaque, calculus, tartar, caries, halitosis, and periodontal diseases such as gingivitis and pyorrhea, but none have been entirely satisfactory. For example some of such materials have been found to be unstable in the presence of the anionic surface active agents generally present in conventional oral preparations. A number of such materials such as the cationic quaternary ammonium agents exert an antibacterial function which undesirably tends to disrupt or destroy the normal microflora of the mouth and/or the digestive system.

Trans-4-(aminomethyl)cyclohexane-1-carboxylic acid, hereinafter referred to as tranexamic acid or TA, of the structural formula

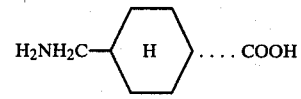

has been shown to be a highly effective agent for controlling, inhibiting or preventing gingivitis and other periodontal diseases, halitosis, and the like; see e.g. Japanese patent application No. 39818/74. This compound is non-antibacterial and unlike antibacterials, it is a specific inhibitor of gingival inflammation, bleeding and/or swelling.

TA is a white crystalline powder having a decomposition temperature of about 380°–390° C. It has characteristic infra red absorption bands at 1637, 1535 and 1383 $cm^{-1}$. It is highly soluble in water, sparingly soluble in heated ethanol, and substantially insoluble in most of the organic solvents. A method for its synthesis or its insolation from cis-trans mixtures thereof is disclosed in U.S. Pat. No. 3,499,925.

Dental caries is a localized, progressively destructive disease of the teeth that starts at the external surface (usually the enamel), with the apparent dissolution of the inorganic components by organic acids. These acids are produced in immediate proximity to the tooth by the enzymatic action of masses of microorganisms (in the bacterial plaque) on carbohydrates. The initial demineralization is followed by an enzymatic destruction of the protein matrix. Cavitation and direct bacterial invasion follow. In the dentin, demineralization of the walls of the tubules is followed by bacterial invasion and destruction of the organic matrix. Untreated dental carie progresses to the pulp, resulting in infection and its sequelae. Stedman's Medical Dictionary, 20th Ed. (1961) p. 268.

It is also well recognized in the art that fluoride ions are effective to inhibit or prevent the formation of caries. Dentifrice compositions containing both TA and fluorine-providing anticaries compounds in combination with other conventional components of such compositions have however been found to be unstable in storage, the compositions turning yellow to dark brown. Attempts to mask this discoloration by adding $TiO_2$ to the compositions resulted in the complete deactivation of the biological activity of the TA.

It is an object of this invention to provide an oral composition containing both TA and a fluorine-providing compound which will not be subject to the above disadvantages. Other objects and advantages will appear as the description proceeds.

The attainment of the above objects is made possible by my discovery that the use in such compositions of a specific flavor mixture of methyl salicylate, menthol, eugenol and cineol prevents the above-described discoloration in storage without significantly diminishing the stability and activity of the TA and fluorine-providing compound.

In accordance with certain of its aspects, this invention relates to an oral composition containing an oral (orally acceptable) vehicle, an effective antigingivitis amount of TA, an effective anticaries amount of a fluorine-providing anticaries agent, and a flavoring amount of a mixture of methyl salicylate, menthol, eugenol and cineol.

The fluorine-providing anticaries compounds useful in the instant oral compositions may be slightly to fully soluble in water. They are characterized by their ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, potassium fluoride, ammonium fluoride, Ca fluoride, a copper fluoride such as cuprous fluoride, zinc fluoride, a tin fluoride such as stannic fluoride or stannous chlorofluoride, barium fluoride, sodium fluorsilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate and mixtures thereof, are preferred.

The amount of the fluorine-providing compound is dependent to some extent upon the type of compound, its solubility, and the type of oral preparation, but it must be a nontoxic amount. In a solid oral preparation, such as toothpaste or toothpowder, an amount of such compound which releases a maximum of about 1% by weight of the preparation is considered satisfactory. Any suitable minimum amount of such compound may be used, but it is preferable to employ sufficient compound to release about 0.005 to 1%, and preferably about 0.1% of fluoride ion. Typically, in the cases of alkali metal fluorides and stannous fluoride, this component is present in an amount up to about 2% by weight, based on the weight of the preparation, and preferably in the range of about 0.05 to 1%. In the case of sodium mono-fluorophosphate (MFP), the compound may be present in an amount up to 7.6%, more typically about 0.5 to about 1% by weight.

In a liquid oral preparation such as a mouthwash, the fluorine-providing compound is typically present in an amount sufficient to release about 0.0005 to about 0.2%, preferably about 0.001 to about 0.1% and more preferably about 0.0013% by weight of fluoride. In general, the instant oral compositions may contain about 0.005 to about 2.0 wt. % of the F-providing compound.

The flavoring mixture essential in the instant oral compositions, in typical proportions of, by weight, about 0.01 to about 3.0%, preferably about 0.5 to about 2.0%, more preferably about 1.0%, contains, by weight, about 55 to about 65%, preferably about 60%, of methyl salicylate, about 30 to about 35%, preferably about 32%, of menthol, about 1 to about 5%, preferably about 3%, of eugenol, and about 3 to about 8%, preferably about 5%, of cineol.

The TA agent may be employed in free acid form or in the form of an orally acceptable salt thereof, preferably water soluble, such as with an alkali metal (e.g. Na or K), ammonium, or $C_1$-$C_8$ mono-, di- or tri-substituted ammonium (e.g. alkanol substituted such as mono-, di- or tri-ethanolammonium) cation. Typically, about 0.001 to about 10.0%, preferably about 0.01 to about 5.0%, and more preferably about 0.03 to about 3.0%, by weight of this TA agent are employed in the oral compositions of this invention.

In certain highly preferred forms of the invention, the oral composition may be substantially liquid in character, such as a mouthwash or rinse. In such a preparation the vehicle is typically a water-alcohol mixture. Generally, the ratio of water to alcohol is in the range of from about 1:1 to about 20:1 preferably from 3:1 to 20:1 and most preferably about 17:3, by weight. The total amount of water-alcohol mixture in this type of preparation is typically in the range of from about 70 to about 99.9% by weight of the preparation. The pH of such liquid and other preparations of the invention is generally in the range of from about 4.5 to about 9 and typically from about 5.5 to 8. The pH is preferably in the range of from about 6 to about 8.0. It is noteworthy that the compositions of the invention may be applied orally at a pH below 5 without substantially decalcifying dental enamel.

Such liquid oral preparations may also contain a surface active agent.

In certain other desirable forms of this invention, the oral composition may be substantially solid or pasty in character, such as toothpowder, a dental tablet, a toothpaste or dental cream. The vehicle of such solid or pasty oral preparations contains polishing material. Examples of polishing materials are water-insoluble sodium metaphosphate, potassium metaphosphate, tricalcium phosphate, calcium pyrophosphate, magnesium orthophosphate, trimagnesium phosphate, calcium carbonate, alumina, hydrated alumina, aluminum silicate, zirconium silicates, silica, bentonite, dihydrated and anhydrous dicalcium phosphates, and mixtures thereof. Preferred polishing materials include crystalline silica having particle sizes of up to 5 microns, a mean particle size of up to 1.1 microns, and a surface area of up to 50,000 $cm^2$/gm., silica gel, complex amorphorus alkali metal aluminosilicate, hydrated alumina, dicalcium phosphate.

Alumina, particularly the hydrated alumina sold by Alcoa as C333, which has an alumina content of 64.9% by weight, a silica content of 0.008%, a ferric oxide content of 0.003%, and a moisture content of 0.37%, at 110° C., and which has a specific gravity of 2.42 and a particle size such that 100% of the particles are less than 50 microns and 84% of the particles are less than 20 microns, is particularly desirable.

When visually clear gels are employed, a polishing agent of colloidal silica, such as those sold under the trademark SYLOID as Syloid 72 and Syloid 74 or under the trademark SANTOCEL as Santocel 100 and alkali metal aluminosilicate complexes are particularly useful, since they have refractive indices close to the refractive indices of gelling agent-liquid (including water and/or humectant) systems commonly used in dentifrices.

Many of the so-called "water-insoluble" polishing materials are anionic in character and also include small amounts of soluble material. Thus, insoluble sodium metaphosphate may be formed in any suitable manner, as illustrated by Thorpe's Dictionary of Applied Chemistry, Volume 9, fourth Edition, pp. 510–511. The forms of insoluble sodium metaphosphate known as Madrell's salt and Kuvrol's salt are further examples of suitable materials. These metaphosphate salts exhibit a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced by washing with water if desired. The insoluble alkali metal metaphosphate is typically employed in powder form of a particle size such that no more than about 1% of the material is larger than 37 microns.

The polishing material is generally present in amounts ranging from about 10 to about 99% by weight of the oral preparation. Preferably, it is present in amounts ranging from about 10 to about 75% in toothpaste, and from about 70 to about 99% in toothpowder.

In the preparation of toothpowders, it is usually sufficient to admix mechanically, e.g., by milling, the various solid ingredients in appropriate quantities and particle sizes.

In pasty oral preparations the above-defined combination of the antigingivitis, anticaries agents and flavor should be compatible with the other components of the preparation. Thus, in a toothpaste, the liquid vehicle may comprise water and humectant typically in an amount ranging from about 10 to about 90% by weight of the preparation. Glycerine, sorbitol, or polyethylene glycol may also be present as humectants or binders. Particularly advantageous liquid ingredients are polyethylene glycol and polypropylene glycol. Also advantageous are liquid mixtures of water, glycerine and sorbitol.

In clear gels where the refractive index is an important consideration, about 3–30% by weight of water, 0 to about 80% by weight of glycerine, and about 20–80% by weight of sorbitol is preferably employed. A gelling agent, such as natural or synthetic gums or gum-like materials, typically Irish moss, sodium carboxymethylcellulose, methyl cellulose, hydroxyethyl cellulose, gum tragacanth, polyvinylpyrrolidone, starch, and preferably hydroxypropyl methyl cellulose and the Carbopols (e.g. 934,940 and 941), etcetera is usually present in toothpaste in an amount up to about 10% by weight, preferably in the range of from about 0.5 to about 5%. In a toothpaste or gel, the liquids and solids are proportioned to form a creamy or gelled mass which is extrudable from a pressurized container or from a collapsible, e.g., aluminum or lead, tube.

The solid or pasty oral preparation which typically has a pH measured on a 20% slurry of about 4.5 to 9, generally about 5.5 to about 8 and preferably about 6 to about 8.0 may also contain a surface active agent.

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a toothpaste will usually be in a collapsible tube, typically aluminum or lined lead, or other squeeze dispenser for metering out the contents, having a label describing it, in substance, as a toothpaste or dental cream.

The oral compositions of this invention may contain a non-soap synthetic sufficiently water soluble organic anionic or nonionic surfactant in concentrations generally ranging from about 0.05 to about 10, preferably about 0.5 to about 5, weight percent, to promote wetting, detersive and foaming properties. U.S. Pat. No. 4,041,149 discloses such suitable anionic surfactants in col. 4, lines 31–38, and such suitable nonionic surfactants in col. 8, lines 30–68 and col. 9, lines 1–12, which passages are incorporated herein by reference thereto.

Various other materials may be incorporated in the oral preparations of this invention, subject to the above. Examples are whitening agents, preservatives, silicones, chlorophyll compounds, and ammoniated material such as urea, diammonium phosphate, and mixtures thereof. These adjuvants, where present, are incorporated in the preparations in amounts which do not substantially adversely affect the properties and characteristics desired.

Sweetening agents, in amounts of about 0.1 to about 5% by weight, may be included in these oral compositions, exemplary of which may be mentioned sucrose, fructose, lactose, maltose, sorbitol, sodium cyclamate, perillartine, APM (aspartylphenylalanine, methyl ester) and saccharin.

The instant oral preparations may be prepared by mixing the components in conventional manner, and applied in the form of a toothpaste or mouthwash or the like to the gingiva and teeth regularly, from about 1 to 3 times daily, at a pH of about 4.5 to about 9, generally about 5.5 to about 8, preferably about 6 to 8.

The following examples are further illustrative of the nature of this invention, but it is understood that the invention is not limited thereto. All amounts and proportions referred to herein and in the appended claims are by weight unless otherwise indicated.

Examples 1–4 in TABLE I below show successively prepared formulations for the attainment of the objects of this invention.

TABLE I

|  | Examples (Weight Percent) | | | |
| --- | --- | --- | --- | --- |
|  | (1) | (2) | (3) | (4) |
| Glycerine | 25.0 | 25.0 | 25.0 | 25.0 |
| Carboxymethyl cellulose | 1.4 | 1.4 | 1.4 |  |
| Na-benzoate | 0.5 | 0.5 | 0.5 | 0.5 |
| Huber silica | 34.0 | 34.0 | 34.0 | 34.0 |
| Sodium lauryl sulfate | 1.5 | 1.5 | 1.5 | 1.5 |
| MFP | 0.76 | 0.76 | 0.76 | 0.76 |
| TA | — | 2.0 | 2.0 | 2.0 |
| TiO$_2$ | — | — | 0.4 | — |
| Flavor A* | 1.0 | 1.0 | 1.0 | — |
| Flavor X** |  |  |  | 1.0 |
| Water | to make 100% | | | |

*Commercial mixture containing at least about 25% of each of carvone, redistilled peppermint, and natural spearmint.
**Mixture of about 60% methyl salicylate, 32% menthol, 3% engenal, and 5% cineol.

Each of the formulations of Examples 1–4 in Table I were subjected to an accelerated aging test for 6 weeks at 120° F., and then observed for resistance to discoloration and tested for fluoride stability and biological (antichemotaxis) activity.

Chemotaxis is the directional movements of leukocytes in response to chemical gradient. This process is thought to account for the accumulation of white blood cells at the site of tissue injury, infectious invasion and under chronic inflammation. Plaque micro-organisms release chemoattractive substances which attract leukocytes from the gingival crevice. The leukocytes release hydrolytic enzyme via reaction with the dental plaque. These enzymes damage the gingivae.

The biological activity of the formulations were determined via the chemotaxis inhibition assay as described by Nelson et al in "Leukocyte Chemotaxis" edited by John I. Gallin and Paul G. Quie (Raven Press, N.Y. 1978). In this assay the ability of the test formulation to inhibit complement induced chemotaxis of polymorphonuclear (PMN) cells is measured, Zymosan activated human serum as chemoattractant. Since sodium lauryl sulfate and flavor interferes with the assay, these materials were first extracted from the aged formulations to be assayed by passing aqueous slurries of the formulations through AG 1×8 Cl⁻ resin and further extracting (5×) with ethyl acetate, after which those formulations containing TA were each normalized to a concentration of 100 micrograms of theoretically available TA.

Table II below shows the results of the discoloration observations and the chemotaxis inhibition assays on the indicated control, placebo (Formulation of Example 1 without MFP) and test formulations, all of which were found to exhibit acceptable fluoride stability.

TABLE II

| Formulation | Mean Chemotactic Activity in Manometer | Inhibition | Color |
|---|---|---|---|
| (a) Zymosan/Serum (Positive Control) | 488 | | OK |
| (b) (a) + TA | 241 | 100% | OK |
| (c) (a) + Placebo | 593 | | OK |
| (d) (a) + Example 1 | 663 | None* | OK |
| (e) (a) + Example 2 | 362 | Fair* | Yellow/ Dark Brown |
| (f) (a) + Example 3 | 663 | None* | OK |
| (g) (a) + Example 4 | 301 | Good* | OK |

*Compared to placebo (c).

The above results show that TA is an excellent inhibitor of chemotaxis (i.e. inhibitor of gingivitis), that the MFP-containing anticaries Example 1 formulation as expected, has no inhibiting effect on chemotaxis, that the MFP/TA-containing Example 2 formulation has a fair inhibiting effect on chemotaxis but discolors badly during aging (storage) apparently due to interaction between the TA and other components in the presence of the MFP, that the addition of $TiO_2$ to the Example 2 formulation (as in the Example 3 formulation) does prevent discoloration but unexpectedly destroys its chemotaxis-inhibiting activity, and that the Example 4 formulation, illustrative of this invention, corresponding to the Example 2 formulation but containing Flavor X instead of Flavor A, is unexpectedly resistant to discoloration and a substantially better inhibitor of chemotaxis than the Example 2 formulation.

EXAMPLE 5

| | Wt. Percent |
|---|---|
| Hydroxypropyl methyl cellulose | 2 |
| Alumina (hydrated) | 49.0 |
| Polyethylene glycol 600 | 33.3 |
| Sodium benzoate | 0.5 |
| Sodium saccharin | 0.2 |
| Sodium lauryl sulfate | 1.5 |
| MFP | 0.76 |
| Tranexamic acid | 1.0 |
| Flavor* | 1.0 |

-continued

| | Wt. Percent |
|---|---|
| Water to make 100% | |

*About 60% methyl salicylate, 32% menthol, 3% eugenol and 5% cineol.

EXAMPLE 6

| | Wt. Percent |
|---|---|
| Insoluble metaphosphate | 48.0 |
| Polyethylene glycol 600 | 35.8 |
| Sodium benzoate | 0.5 |
| Sodium saccharin | 0.2 |
| Sodium laurylsulfate | 1.5 |
| Flavor* | 1.0 |
| Colloidal silica | 6.0 |
| MFP | 0.76 |
| Tranexamic acid | 1.5 |
| Water to make | 100% |

*About 60% methyl salicylate, 32% menthol, 3% eugenol and 5% cineol.

Examples 5 and 6 illustrate dentifrice formulations according to the invention. Other conventional components may be substituted or added as disclosed hereinbefore; e.g. polyethylene glycol 600 may be replaced by other gelling agents such as Pluronic F-127 (polyoxyethylenated polyoxypropylene), Laponite (Mg-Al-Si clay), or Carbopol 940.

I claim:

1. An oral composition for promoting oral hygiene containing an oral vehicle and, approximately by weight, 0.001 to 10.0% of tranexamic acid as antigingivitis agent, 0.005 to 2.0% of a fluorine-providing anticaries agent, and 0.01 to 3.0% of a flavoring mixture, which mixture consists essentially of, approximately by weight, 55 to 65% of methyl salicylate, 30 to 35% of menthol, 1 to 5% of eugenol, and 3 to 8% of cineol.

2. The oral composition of claim 1 containing about 0.5 to about 1.0% by weight of sodium monofluorophosphate.

3. The oral composition of claim 1 wherein said mixture is composed of, approximately by weight, 60% methyl salicylate, 32% of menthol, 3% of eugenol, and 5% of cineol.

4. The oral composition of claim 3 containing about 0.5 to about 1.0% by weight of sodium monofluorophosphate.

5. The oral composition of claims 3, 4 or 2 which is a mouthwash having a pH of about 4.5 to about 9 and an aqueous-alcohol vehicle.

6. The oral composition of claims 3, 4 or 2 which is a toothpaste having a pH of about 4.5 to about 9 containing a liquid vehicle, a gelling agent and a dentally acceptable polishing material.

7. A method of improving oral hygiene comprising applying to the oral cavity an effective amount of an oral composition as defined in claims 3, 4 or 2.

* * * * *